United States Patent
Nam et al.

(10) Patent No.: US 9,662,179 B2
(45) Date of Patent: May 30, 2017

(54) APPARATUS AND METHOD FOR CORRECTING THREE DIMENSIONAL SPACE-ANGLE OF DRILL FOR DENTAL HAND PIECE

(71) Applicants: Yoon Nam, Chungcheongnam-do (KR); Kwangwoo Jeong, Seoul (KR)

(72) Inventors: Yoon Nam, Chungcheongnam-do (KR); Kwangwoo Jeong, Seoul (KR)

( * ) Notice: Subject to any disclaimer, the term of this patent is extended or adjusted under 35 U.S.C. 154(b) by 0 days.

(21) Appl. No.: 14/845,295

(22) Filed: Sep. 4, 2015

(65) Prior Publication Data

US 2016/0067010 A1    Mar. 10, 2016

(30) Foreign Application Priority Data

Sep. 5, 2014  (KR) .................. 10-2014-0118985

(51) Int. Cl.
*A61C 1/08* (2006.01)
*A61C 1/00* (2006.01)
*A61B 19/00* (2006.01)
*A61B 34/20* (2016.01)

(52) U.S. Cl.
CPC .......... *A61C 1/084* (2013.01); *A61B 19/5244* (2013.01); *A61B 34/20* (2016.02); *A61C 1/0023* (2013.01); *A61C 1/082* (2013.01)

(58) Field of Classification Search
CPC ......... A61C 1/082; A61C 1/084; A61C 1/085; A61C 1/0023; A61B 19/5244; A61B 34/20
USPC .......................................................... 433/27
See application file for complete search history.

(56) References Cited

U.S. PATENT DOCUMENTS

| 4,824,367 | A | * | 4/1989 | Rosenstiel | G01C 9/00 433/27 |
|---|---|---|---|---|---|
| 6,000,939 | A | * | 12/1999 | Ray | A61C 1/082 433/27 |
| 7,346,417 | B2 | * | 3/2008 | Luth | A61B 34/20 128/920 |
| 2004/0157188 | A1 | * | 8/2004 | Luth | A61B 34/20 433/75 |
| 2005/0163342 | A1 | * | 7/2005 | Persky | A61B 6/14 382/103 |
| 2011/0311944 | A1 | * | 12/2011 | Earthman | A61B 9/00 433/119 |
| 2012/0319859 | A1 | * | 12/2012 | Taub | A61C 1/082 340/689 |

(Continued)

*Primary Examiner* — Nicholas Lucchesi
(74) *Attorney, Agent, or Firm* — Revolution IP, PLLC

(57) ABSTRACT

An apparatus for correcting a three dimensional space-angle of a drill for a dental hand piece, including: a housing provided on a fixing unit of the dental hand piece; a first sensing unit for measuring an angle of the housing in real-time; a second sensing unit for measuring an angle of a head portion or jaw of the patient in real-time; an operating unit for calculating the three-dimensional space angle of the drill; a setting unit for setting a reference three-dimensional space angle of the drill with respect to the tooth structure as a three-dimensional space angle that the operator is wanting among the three-dimensional space angles of the operating unit; and a display unit for displaying an alert message when the three-dimensional space angle of the operating unit deviates from a predetermined range of the reference three-dimensional space angle.

17 Claims, 4 Drawing Sheets

(56) References Cited

U.S. PATENT DOCUMENTS

| | | | |
|---|---|---|---|
| 2013/0209953 A1* | 8/2013 | Arlinsky | A61C 1/082 433/27 |
| 2013/0244196 A1* | 9/2013 | Goodacre | A61C 8/009 433/27 |
| 2013/0316297 A1* | 11/2013 | Sogo | A61C 1/084 433/27 |
| 2014/0272773 A1* | 9/2014 | Merritt | A61B 5/0088 433/29 |
| 2014/0343395 A1* | 11/2014 | Choi | A61B 5/4851 600/409 |
| 2015/0182296 A1* | 7/2015 | Daon | A61B 19/5244 600/424 |
| 2016/0135904 A1* | 5/2016 | Daon | A61B 6/032 600/424 |
| 2016/0235483 A1* | 8/2016 | Zeilhofer | A61C 3/02 |

* cited by examiner (a)

(b)

APPARATUS AND METHOD FOR CORRECTING THREE DIMENSIONAL SPACE-ANGLE OF DRILL FOR DENTAL HAND PIECE

CROSS-REFERENCE TO RELATED APPLICATIONS

This U.S. non-provisional patent application claims priority under 35 U.S.C. §119 of Korean Patent Application No. 10-2014-0118985, filed on Sep. 5, 2014, the entire contents of which are hereby incorporated by reference.

BACKGROUND OF THE INVENTION

The present invention disclosed herein relates to an apparatus and method for correcting a three dimensional space-angle of a drill for a dental hand piece.

In general, a dental hand piece is used for cutting or drilling a tooth or an alveolar bone. The dental hand piece is provided at its front end with a rotatable drill.

The demands for accurate dental surgical procedure using the dental hand are increasing. Technology for satisfying demands for a teeth grinding surgical procedure and an implant placement surgical procedure that are two axes of a modern dental surgical procedure has been greatly developed. The accurate dental surgical procedure improves surgical completion, increases a life span of the dental prosthetics, and reduces the time spent for operating the dental surgical procedure. Furthermore, the accurate dental surgical procedure enables a minimally invasive technique that reduces complications after surgery. Particularly, the accuracy of the angle of the dental hand piece is more important for forming an abutment of a metal-ceramic crown and placing the implant.

Sufficient maintenance and proper resistance form for preventing the performance of the metal-ceramic crown from being removed are essential. The maintenance of a cast restoration is determined by a convergence angle of a grinded portion, a surface area, an inner surface roughness of the crown, and the like. Among these, the convergence angle is a primary factor and many researches for the convergence angle have been done. The convergence angle means an angle between extensions of two shaft walls that are formed on the abutment through the grinding of the teeth and faces each other. The convergence angle has an influence on maintenance of restoration. It is known that the optimal convergence angle is between 5 degrees and 12 degrees. In addition, the accuracy of the convergence angle is also important for the best esthetic appreciation for the dental implant placement and the long life span of the implant. The implant placement angle determines the direction of occlusal force applied to the implant and the retention force of the restorations. Especially, when two or more dental implants are placed, the placement angles between different implants critically determine the performance and life span of the implants.

As described above, the accurate angle in the dental surgical procedure is very important. However, the existing dental hand piece cannot satisfy such importance in the dental surgical procedure. This is well shown in the convergence angle research of the abutment for the metal-ceramic crown. Analogy results of the convergence angles of the abutments of 478 metal-ceramic crowns in the practical surgical procedure show that the mean convergence angle is 21 degree and there are big differences in the convergence angles according to dentists. Other researches also report that the convergence angle in the grinding of the abutment is 14-20 degrees. This supports the above facts. These values significantly deviate from the ideal value. The increase of the convergence angle results in the reduction of the mean retention force regardless of the kind of the cement used. The inferiority in fixing-type prosthetics is caused by ceramic fracture (16%) and then by defective adhesiveness (15.1%) due to low retention force. The defective adhesiveness can be prevented by preventing the increase of the convergence angle.

The above-described inaccuracy is resulted from the operator using the existing hand piece who depends on her/his motion skill and space perception ability. Particularly, it is very difficult to reach an optimal three-dimensional angle of the hand piece drill in a three-dimensional space due to physiological limitation of the human. Except for a few master dentists having a unique talent and experiences for many years, most of the dentists have difficulty in reproducing the optimal dental surgical procedure. In order to overcome such limitation and improve overall dental surgical procedure quality, there is a need to objectively measure the dental surgical procedure and develop an auxiliary apparatus showing such objective measurement.

To this end, new methods cooperating with computers have been developed. Particularly, the implant placement surgery has reached the level of a computer guided navigation system that can setup a pre-operation plan through a 3D CT and planning software and can implement the pre-operation plan using surgical guide and optical tracking apparatuses. Furthermore, there is a method using an electromagnetic tracker, and an instrument like a parallel-A-prep that enables direct surveying in the mouth upon tooth grinding is being sold on the market.

In spite of such technical development, many limitations must be overcome in order to utilize the computer guided navigation system in the clinic practice. In order to use the above-described surgical guide or the optical tracking, a bulky and expensive hardware and a complicated process are required. In addition, reference bodies for the surgical guide and the optical tracking can reproduce and must be perfectly fit to patients, it is actually impossible to guarantee in all operation circumstances. Especially, in the surgical guide, a gap between a drill and a hole inevitably exists to supply cooling water to an implant placing portion. Accordingly, there may be an angle error that is greater at an alveolar coronal than at an alveolar apical. In addition, the method using the electromagnetic tracker has a limitation in that the accuracy is relative low and a measured value of metal prosthetics in the mouth may be unstable. When the navigation system is used, the operation time increases and thus the risk also increases because the referencing time in the implant surgical procedure and the navigation time are long. For the parallel-A-Prep that is used for the accurate path of insertion when the tooth is grinded, the volume of the apparatus is too big and the installation is complicated.

SUMMARY OF THE INVENTION

The present invention provides an apparatus and method for correcting a three dimensional space-angle of a drill for a dental hand piece, which are not limited in use by an ambient environment while not using the reference body for tracking, an additional camera, and the like.

The present invention also provides an apparatus and method for correcting a three dimensional space-angle of a drill for a dental hand piece, which can reduce factors that may disturb the operator by miniaturization and simplification, are not limited in use by a circumferential environment such as the metal prosthetics in the mouth, maintain accuracy, are inexpensive, and intuitional and easy in use.

Embodiments of the present invention provide apparatuses for correcting a three dimensional space-angle of a drill for a dental hand piece for a tooth structure including hard and soft tissues in an oral and maxillofacial area including a jawbone and teeth of a patient, the apparatuses including: a housing provided on a fixing unit of the dental hand piece; a first sensing unit for measuring an angle of the housing in real-time; a second sensing unit for measuring an angle of a head portion or jaw of the patient in real-time; an operating unit for primarily correcting the angle of the housing measured by the first sensing unit with reference to the angle of the drill and secondarily correcting an angle of the drill, which is primarily corrected, with reference to an angle correcting value of the drill with respect to the tooth structure considering the angle measured by the second sensing unit, thereby calculating the three-dimensional space angle of the drill; a setting unit for setting a reference three-dimensional space angle of the drill with respect to the tooth structure as a three-dimensional space angle that the operator is wanting among the three-dimensional space angles of the operating unit; and a display unit for displaying an alert message when the three-dimensional space angle of the operating unit deviates from a predetermined range of the reference three-dimensional space angle.

In other embodiments, the housing may be detachably fixed on the fixing unit of the dental hand piece. Alternatively, the housing may have a hollow portion that is detachably fitted in the fixing unit of the dental hand piece.

In still other embodiments, the housing may be integrally formed with the fixing unit of the dental hand piece.

In even other embodiments, a vibration-preventing member may be provided on an inner circumferential surface of the hollow portion.

In yet other embodiments, each of the first and second sensing unit may be an electronic sensor.

In further embodiments, each of the first and second sensing unit may be an electronic sensor having a gyro sensor and an acceleration sensor.

In still further embodiments, the display unit may include a wire or wireless communication module transmitting the alert message to an external terminal.

In even further embodiments, the display unit may include a first lamp displaying such that the drill is inclined to a right direction that is a +X-axis, a second lamp displaying such that the drill is inclined to a lower direction that is a −Y-axis, a third lamp displaying such that the drill is inclined to a left direction that is a −X-axis, and a fourth lamp displaying such that the drill is inclined to an upper direction that is a +Y-axis.

In yet further embodiments, each of the first, second, third, and fourth lamps may be provided as a sect having at least one color light.

In other embodiments of the present invention, the housing may be formed in a hollow cylindrical shape, the first, second, third, and fourth lamps may be provided as a one lamp unit, and a plurality of the lamp units may be disposed along an outer circumference of the housing at a predetermined distance.

In still other embodiments of the present invention, the setting unit further includes a switch and the reference three-dimensional space angle may be set as an angle that is set by the operator when the operator presses the switch.

In even other embodiments of the present invention, the switch may be provided on a pedal so that the operator can step.

In other embodiments of the present invention, methods for correcting a three dimensional space-angle of a drill for a dental hand piece for a tooth structure including hard and soft tissues in an oral and maxillofacial area including a jawbone and teeth of a patient, include: measuring an angle of the dental hand piece and an angle of a head portion or jaw of the patient in real-time; calculating the three-dimensional space angle of the drill by primarily correcting the angle of the dental hand piece as an angle of the drill and secondarily correcting an angle the drill, which is primarily corrected, with reference to an angle correcting value of the drill with respect to the tooth structure considering the angle of the head portion; setting a reference three-dimensional space angle of the drill with respect to the tooth structure as a three-dimensional space angle that the operator is wanting among the three-dimensional space angles calculated; and displaying an alert message when the calculated three-dimensional space angle deviates from a predetermined range of the reference three-dimensional space angle.

In other embodiments, in the measuring in real-time, in order to correct the angle of the drill by measuring the angle of the dental hand piece in real-time, the following determinant may be used:

$$\begin{bmatrix} x \\ y \\ z \end{bmatrix} = \begin{bmatrix} \cos\theta & 0 & \sin\theta \\ 0 & 1 & 0 \\ -\sin\theta & 0 & \cos\theta \end{bmatrix} \begin{bmatrix} x' \\ y' \\ z' \end{bmatrix}$$

where, the x, y, and z indicate orientation of the drill, the x', y', and z' indicate orientation of the fixing unit of the dental hand piece, and the θ denotes an angle between a first imaginary line extending in a longitudinal direction of the fixing unit and a second imaginary line perpendicular to the drill.

In still other embodiments, in the displaying of the alert message, the alert message may be displayed such that, when the three-dimensional space angle deviates from the predetermined range of the reference three-dimensional space angle as the drill is inclined to a right direction that is a +X-axis, the drill is inclined to a left direction that is a −X-axis; the alert message may be displayed such that, when the three-dimensional space angle deviates from the predetermined range of the reference three-dimensional space angle as the drill is inclined to a lower direction that is a −Y-axis, the drill is inclined to an upper direction that is a +Y-axis; the alert message may be displayed such that, when the three-dimensional space angle deviates from the predetermined range of the reference three-dimensional space angle as the drill is inclined to the left direction that is the −X-axis, the drill is inclined to the right direction that is the +X-axis; and the alert message may be displayed such that, when the three-dimensional space angle deviates from the predetermined range of the reference three-dimensional space angle as the drill is inclined to the upper direction that is the +Y-axis, the drill is inclined to the lower direction that is the −Y-axis.

In even other embodiments, when the three-dimensional space angle of the drill is inclined in a first side and thus deviates from the predetermined range of the reference three-dimensional space angle, in order to incline the blade in a second side opposite to the first side, one of the lamps, which has a first color and disposed at the second side, may keep emitting light and another one of the lamps, which has the first color and disposed on the first side, may keep blinking.

In yet other embodiments, the displaying of the alert message may include transmitting the alert message to an external message through a wire or wireless communication.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art.

Hereinafter, it will be described about an exemplary embodiment of the present invention in conjunction with the accompanying drawings.

Figure 1:
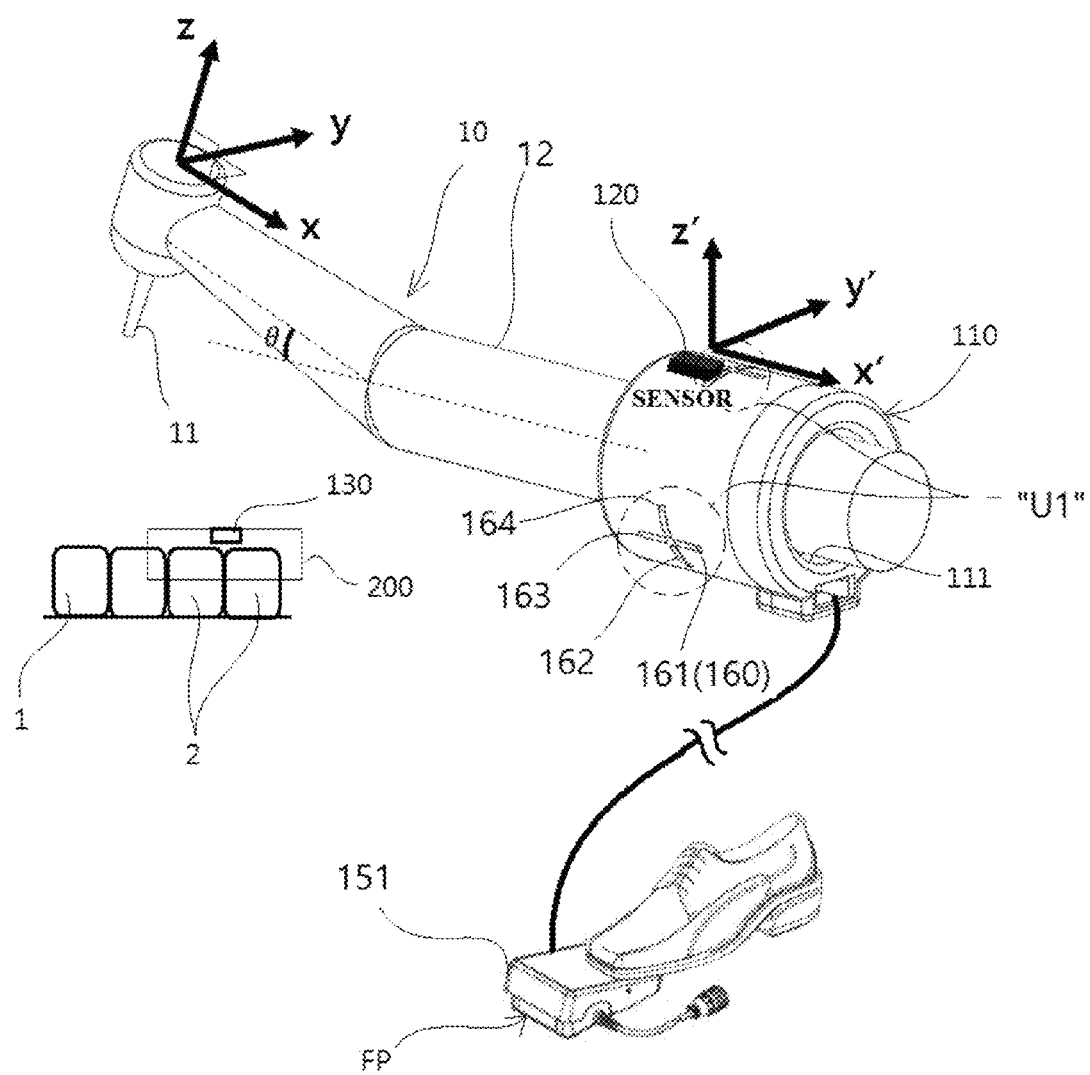
FIG. 1 is a view illustrating a state where an apparatus for correcting a three dimensional space-angle of a drill according to an exemplary embodiment of the present invention is installed on a dental hand piece.
Figure 2:
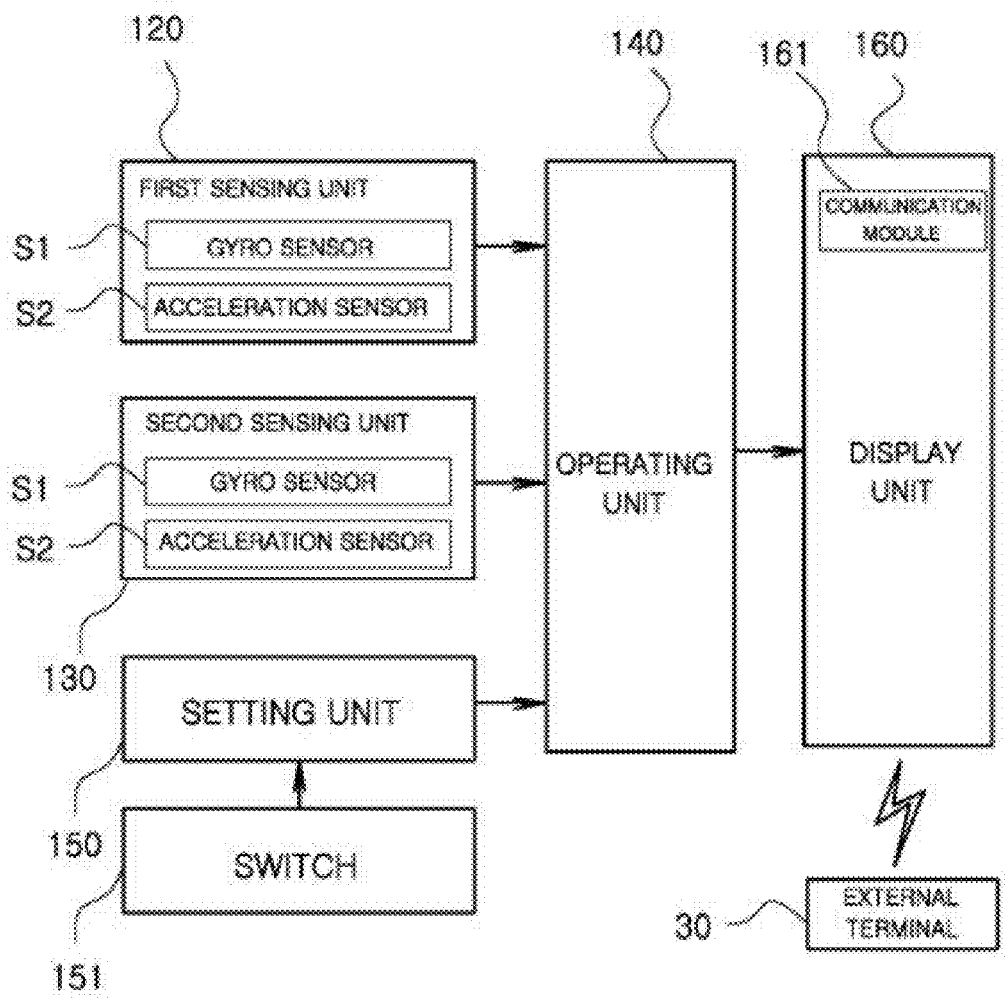
FIG. 2 is a block diagram of the apparatus for correcting a three dimensional space-angle of FIG. 1.
Figure 3:
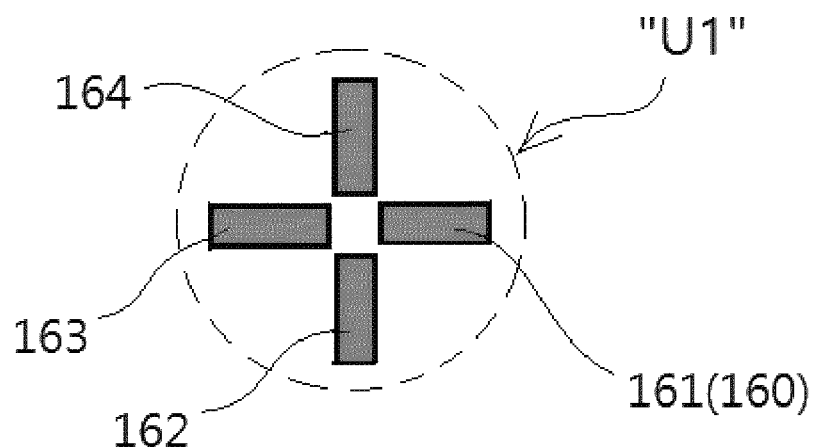
FIG. 3 is a diagram of a lamp unit of a display unit of the apparatus illustrated in FIG. 1.
Figure 3:
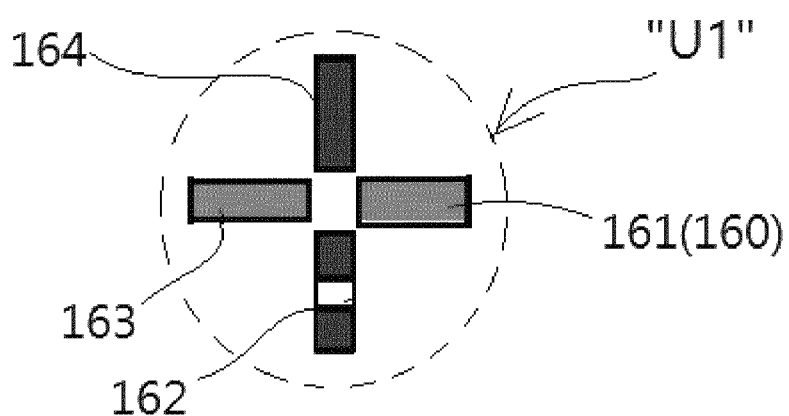

FIG. 1 is a diagram illustrating a state where an apparatus for correcting a three dimensional space-angle of a drill according to an exemplary embodiment of the present invention is installed on a dental hand piece, FIG. 2 is a block diagram of the apparatus for correcting a three dimensional space-angle of FIG. 1, and FIG. 3 is a diagram of a lamp unit of a display unit of the apparatus illustrated in FIG. 1.

As shown in FIGS. 1 to 3, an apparatus for correcting a three dimensional space-angle of a drill according to an exemplary embodiment of the present invention is for a tooth structure (hereinafter, referred to as "teeth 1") including hard and soft tissues in the oral and maxillofacial area including the teeth and the jawbone of a patient. The apparatus includes a housing 110, a first sensing unit 120, a second sending unit 130, an operation unit 140, a setting unit 150, and a display unit 160.

The housing 110 is provided on a fixing unit 12 of a dental hand piece 10 and with the first sensing unit 120 and the display unit 160. For example, the housing 110 is designed such that, when an operator (dentist) grasps the fixing unit 12 of the dental hand piece 10 as if he/she hold a pencil using the thumb and index finger, the housing 110 is located in a space defined between the thumb and index finger. For example, the housing 110 may be detachably provided on the fixing unit 12 of the dental hand piece 10. Alternatively, the housing 110 may be integrally formed with the fixing unit 12 of the dental hand piece 10. Especially, when the housing 110 is detachably provided on the fixing unit 12 of the dental hand piece 10, the housing 110 can be detached when the dental hand piece 10 is washed. Therefore, it can be prevented that the electronic devices such as the first sensing unit 120 and the display unit 160 are short-circuited. Furthermore, as shown in FIG. 1, the housing 110 the housing 110 may be detachably fitted to the fixing unit 12 of the dental hand piece 10. In addition, when the dental hand piece 10 is driven, a drill 11 provided on a front end thereof rotates. At this point, vibration occurs. The first sensing unit 120 and the like may be affected by the vibration. To prevent this, a vibration-preventing member (not shown) may be provided on an inner circumferential surface of a hollow portion 111.

The first sensing unit 120 measures an angle of the housing 110 in real-time. The first sensing unit 120 may be an electronic sensor or, as shown in FIG. 2, may include a gyro sensor S1 and an acceleration sensor S2. The gyro and acceleration sensors S1 and S2 are used to measure a three-dimensional space angle of the hand piece drill. The acceleration sensor S2 is used to measure a relative acceleration to the acceleration of gravity, and the gyro sensor S1 obtains a rotational distance by integrating a measured angular velocity. Thus, the angle of the housing 110 can be accurately measured using basic information evaluating the three-dimensional space angle of the drill 11 of the dental hand piece 10. For example, an MPU-6050 module loaded with the acceleration and gyro sensors S2 and S1 may be used.

The second sensing unit 130 is for measuring an angle of a head region of the patient. The second sensing unit 130 may be fixed on the jaw or the teeth that is not treated by a mouth piece 200. The second sensing unit 130 is provided in the case the head or jaw of the patient moves. When the head or jaw of the patient moves, the angle of the teeth 1 to be treated may be changed. Accordingly, when the change of the angle of the teeth 1 is accurately measured, an angle correction value of the drill with respect to the teeth 1 can be accurately provided through the operating unit 140.

Furthermore, like the first sensing unit 120, the second sensing unit 130 may be an electronic sensor or, as shown in FIG. 2, includes a gyro sensor S1 and an acceleration sensor S2. The gyro and acceleration sensors S1 and S2 are used to measure a three-dimensional space angle of the hand piece drill. The acceleration sensor S2 is used to measure a relative acceleration to the acceleration of gravity and the gyro sensor S1 measures a rotational distance by integrating a measured angular velocity. Therefore, the angle of the head region or the teeth of the jaw can be accurately measured using basic information evaluating the three-dimensional space angle of the drill 11 of the dental hand piece 10. For example, the MPU-6050 module loaded with the acceleration and gyro sensors S2 and S1 may be used.

The operating unit 140 primarily corrects the angle of the housing 110 measured by the first sensing unit 120 with reference to the angle of the drill 11. Then, the operating unit 140 secondarily corrects an angle of the drill 11, which is primarily corrected, with reference to an angle correcting value of the drill 11 with respect to the teeth 1 to be treated considering the angle of the teeth 2 of the head region (or jaw) that is measured by the second sensing unit 130, thereby calculating the three-dimensional space angle of the drill 11 with respect to the teeth 1. That is, the operating unit is designed to calculate the 3-dimension space angle of the drill by correcting the measured values attained by the first and second sensing units 120 and 130 through a correcting algorithm such as the Kalman filter algorithm.

The setting unit 150 is for setting a reference three-dimensional space angle of the drill 11 to the teeth 1 as a three-dimensional angle the operator desires among the three-dimensional space angles calculated by the operating unit 140. When the operator presses a switch 151 after he/she sets a desired angle of the drill 11, the desired angle is set as the reference three-dimensional space angle. As shown in FIG. 1, the switch 151 may be provided on a pedal so that the operator steps the same using his/her feet. The switch 151 may be connected to the setting unit 150 by a wire or a wireless communication (not shown). Although not shown in the drawings, electric power may be supplied through a pivot portion (not shown) pivotally coupled to a rear end of the fixing unit 12 of the dental hand piece 10.

The display unit 160 displays an alert massage when the three-dimensional space angle of the operating unit 140 deviates from a predetermined range of the reference three-dimensional space angle. For example, as shown in FIG. 2, the display unit 160 may include a wire or wireless communication module 161. The communication module 161 may transmit the alert massage to an external terminal such as a Google glass.

In another example, as shown in FIG. 3, the display unit 160 may include a first lamp 161 displaying such that the drill 11 is inclined to a right direction that is +X-axis direction, a second lamp 162 displaying such that the drill 11 is inclined to a lower direction that is −Y-axis, a third lamp 162 displaying such that the drill 11 is inclined to a left direction that is −X-axis, and a fourth lamp 164 displaying such that the drill 11 is inclined to an upper direction that is +Y-axis. Furthermore, each of the first, second, third, and fourth lamps 161, 162, 163, and 164 may be provided with a light having at least one color as one set. Also, as shown in FIG. 1, the housing 110 may be formed in a hollow cylinder and the first, second, third and fourth lamps 161, 162, 163, 164 may be provided as one lamp unit U1. A plurality of the lamp units U1 may be arranged along a circumference of the outer surface of the housing 110. In addition, the lamp having a first color and the lamp having a second color may be light emitting diodes (LEDs). Meanwhile, when the drill 11 rotates about a Z-axis that is an axis of the drill 11, the three-dimensional space angle of the hand piece drill is not changed. Therefore, the Z-axis is not shown. Since the angle correction with respect to the X and Y-axes is actually displayed on the display unit 160, it is convenient to use and to perform the clinic as compare with a case where the Z-axis is displayed together.

In an example showing an exemplary operation of the display unit 160, as shown in FIG. 3A, when the drill 11 is within a predetermined range of the reference angle, the first, second, third, and fourth lamps 161, 162, 163, and 164 that are spaced away from each other by 90 degree are turned ON and keep emitting a green light. Accordingly, since all of the lamps 161, 162, 163, and 164 emit the green light, the operator can easily identify accurate information with respect to the X, −X, Y, −Y-axes. In addition, as shown in FIG. 3B, when the three-dimensional space angle of the drill 11 is inclined to the −Y-axis and thus deviates from the predetermined range, the fourth lamp 164 provided on the +Y-axis keeps emitting a red light and the second lamp 162 provided on the −Y-axis brinks a red light so that the operator inclines the blade to the +Y-axis. Accordingly, the operator may incline the drill in the +Y-axis on which the red light is continuously turned on. The display unit operates in the same manner with respect to other X-axis, Alternatively, although not shown in the drawings, the display unit 160 may be set such that when all of the lamps 161, 162, 163, and 164 are turned on, it is regarded that the angle is within the predetermined range. When one of the lamps blinks, the operator inclines the drill toward the blinking lamp.

Hereinafter, a method for correcting a three-dimensional space angle of the dental hand piece drill according to an exemplary embodiment of the present invention with reference to FIG. 4.

Figure 4:
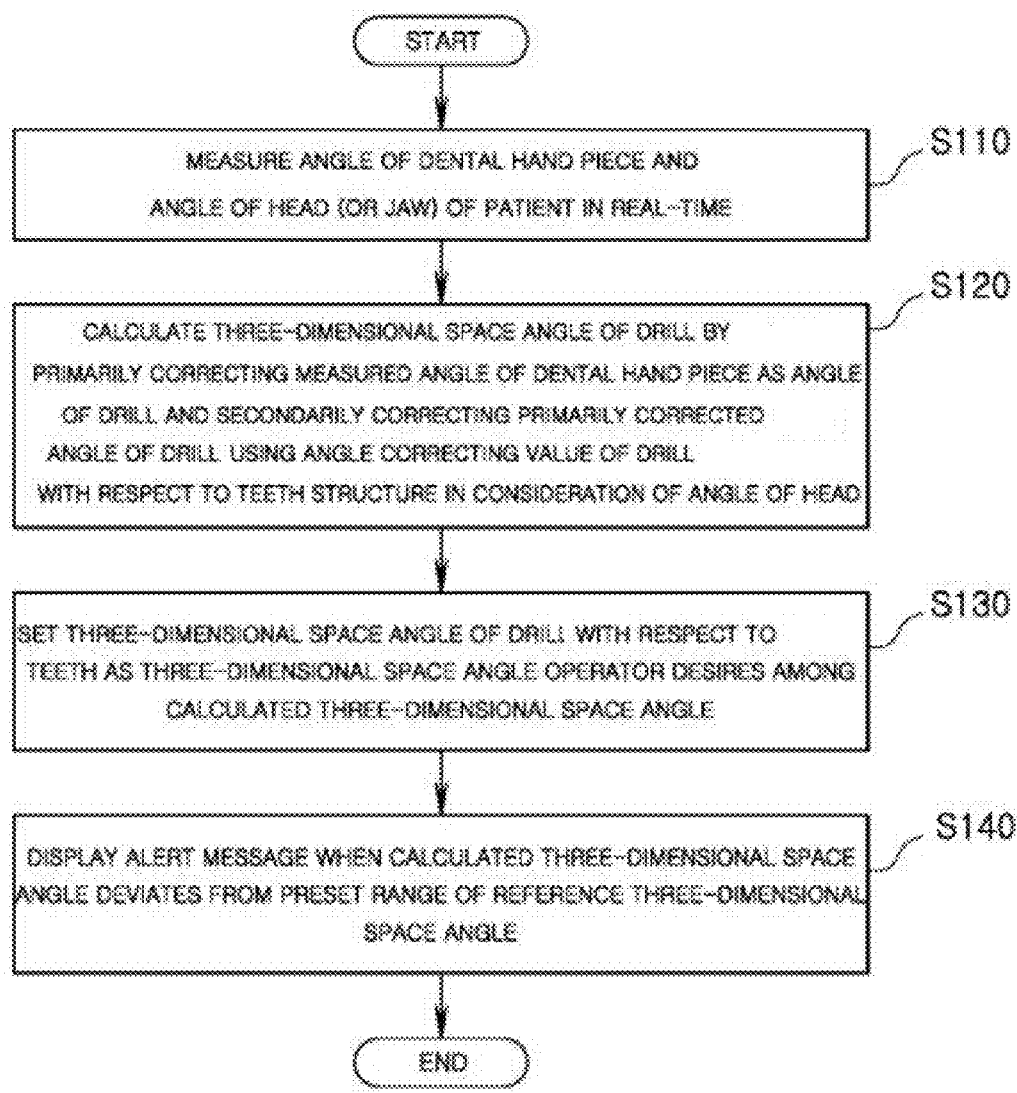
FIG. 4 is a flowchart illustrating a method for correcting a three dimensional space-angle of a drill according to an exemplary embodiment of the present invention.

FIG. 4 is a flowchart illustrating a method for correcting a three dimensional space-angle of a drill according to an exemplary embodiment of the present invention.

A method for correcting a three dimensional space-angle of a drill according to an exemplary embodiment of the present invention is for a tooth structure (hereinafter, referred to as "teeth 1") including hard and soft tissues in the oral and maxillofacial area including the teeth and the jawbone of a patient. First, an angle of the dental hand piece 10 (e.g., an angle of the housing 110) and an angle of the head region (or jaw) (e.g., an angle of the teeth that is not required to be treated) are measured in real-time (S110). For example, the angles may be measured by a set of the gyro and acceleration sensors S1 and S2 that are provided at each location. The gyro and acceleration sensors S1 and S2 measuring three-axis measure a relative acceleration with respect to the acceleration of gravity and attain a rotational distance by integrating the measured angular velocity. Thus, the angle of the housing 110 can be accurately measured using basic information evaluating the three-dimensional space angle of the drill 11 of the dental hand piece 10. For example, an MPU-6050 module loaded with the acceleration and gyro sensors S2 and S1 may be used.

Next, the angle of the housing 110 measured by the first sensing unit 120 with reference to the angle of the drill 11 is primarily corrected and then the angle of the drill 11, which is primarily corrected, with reference to an angle correcting value of the drill 11 with respect to the teeth 1 considering the angle of the head region (or jaw (i.e., the angle of the teeth that is not required to be treated) are secondarily corrected in real-time, thereby calculating the three-dimensional space angle of the drill 11 with respect to the teeth 1 (S120). For example, the 3-dimension space angle of the drill can be calculated by correcting the measured values attained by the first and second sensing units 120 and 130 through a correcting algorithm such as the Kalman filter algorithm. In addition, in Step S120, in order to correct the angle of the drill 11 by measuring the angle of the dental hand piece 10 in real-time, the following determinant may be used:

$$\begin{bmatrix} x \\ y \\ z \end{bmatrix} = \begin{bmatrix} \cos\theta & 0 & \sin\theta \\ 0 & 1 & 0 \\ -\sin\theta & 0 & \cos\theta \end{bmatrix} \begin{bmatrix} x' \\ y' \\ z' \end{bmatrix}$$

where, with reference to FIG. 1, the x, y, and z indicate orientation of the drill, the x', y', and z' indicate orientation of the fixing unit of the dental hand piece, and the θ denotes an angle between a first imaginary line extending in a longitudinal direction of the fixing unit and a second imaginary line perpendicular to the drill.

A reference three-dimensional space angle of the drill 11 to the teeth 1 is set as a three-dimensional angle the operator desires among the three-dimensional space angles calculated (S130). For example, when the operator presses a switch 151 of the setting unit 150 after he/she sets a desired angle of the drill 11, the desired angle is set as the reference three-dimensional space angle.

An alert massage is displayed when the calculated three-dimensional space angle deviates from a predetermined range of the reference three-dimensional space angle (S140). Describing the displaying method, when the three-dimensional space angle deviates from the predetermined range of the reference three-dimensional space angle as the three-dimensional space angle is inclined to a right direction that is a +X-axis, the message is displayed such that the three-dimensional angle is inclined to a left direction that is a −X-axis. When the three-dimensional space angle deviates from the predetermined range of the reference three-dimensional space angle as the three-dimensional space angle is inclined to a lower direction that is a −Y-axis, the message is displayed such that the three-dimensional angle is inclined to an upper direction that is a +Y-axis. When the three-dimensional space angle deviates from the predetermined range of the reference three-dimensional space angle as the three-dimensional space angle is inclined to a left direction that is a −X-axis, the message is displayed such that the three-dimensional angle is inclined to a right direction that is a +X-axis. When the three-dimensional space angle deviates from the predetermined range of the reference three-dimensional space angle as the three-dimensional space angle is inclined to an upper direction that is a +Y-axis, the message is displayed such that the three-dimensional angle is inclined to a lower direction that is a −Y-axis. In more detail, as shown in FIG. 3A, when the drill 11 is within a predetermined range of the reference angle, the first, second, third, and fourth lamps 161, 162, 163, and 164 that are spaced away from each other by 90 degree are turned ON and keep emitting a green light. Accordingly, since all of the lamps 161, 162, 163, and 164 emit a second color light, the operator can easily identify accurate information with respect to the X, −X, Y, −Y-axes. In addition, as shown in FIG. 3B, when the three-dimensional space angle of the drill 11 is inclined to the −Y-axis and thus deviates from the predetermined range, the fourth lamp 164 provided on the +Y-axis keep emitting a first color light and the second lamp 162 provided on the −Y-axis brinks the first color light so that the operator inclines the blade to the +Y-axis where the first color light is continuously emitted. Then, the operator inclines the drill in the +Y-axis. The display unit operates in the same manner with respect to other axes, Hereinafter, the effect of the apparatus for correcting the three-dimensional angle of the dental hand piece drill according to the exemplary embodiment of the present invention will be described.

Verification of the Apparatus for Correcting the Three-Dimensional Space Angle of the Dental Hand Piece Drill According to the Exemplary Embodiment of the Present Invention The effect of the apparatus for correcting the three-dimensional space angle to be verified is as follows: First, the three-dimensional space angle for the abutment can be improved as compared with the existing apparatuses. Second, the angle can be corrected in response to the patient motion. Third, the surgical operation time can be reduced as compared with the existing apparatuses.

Test 1: Abutment Forming Evaluation in Standstill State

In order to exclude an affection by the leaning effect, the test was performed by two groups, the first group (10 Students and 2 skilled dentists) using the inventive apparatus first and the second group (10 students and 2 skilled dentists) using the inventive apparatus second. All conditions of the test for the first and second groups using the inventive apparatus were same each other except for the procedure of the tooth preparation. Upper and lower jaw dentiforms from which teeth model No. 24 and 35 were extracted are mounted on a dental phantom. A teeth model No. 24 that was milling-treated about 6-degree inclination in advance was used as a standard reference. At this point, the operator was instructed not to manipulate a location and direction of the dental phantom.

A. Group Using the Three-Dimensional Space Angle Correcting Apparatus

This group inputs a three-dimensional space angle of the standard reference tooth in the apparatus and then formed a depth groove with reference to this angle, after which this group performed the grinding of an axial wall for Nos. 24-26 3-unit PFM Bridge. While grinding the teeth, this group kept adjusting the three-dimensional space angle by utilizing angle information displayed on the apparatus. A total tooth preparation time was measured.

B. Conventional Tooth Preparation Group

The tooth preparation of the axial wall for a teeth No. 26 3-unit PFM bridge was performed with reference to the standard reference tooth according to the conventional art. A total tooth preparation time was measured.

Test 2: Evaluation for Correction with Respect to Patient Movement

The standard reference angle was measured when the dental phantom is at a supine position and then a guiding groove was formed on an abutment No. 26. The head of the dental phantom was rotated by −60-degree and a new guiding groove was formed on another surface of the teeth No. 26. The parallel of the grooves are compared with each other.

Geometrical information for the teeth model No. 26 where the abutment was formed in the tests 1 and 2 is digitalized by a 3D-scanner (4DCULTURE, Daegu, Korea). Then, a mean convergence angle of the axial wall and the convergence angle of each face were measured by image analysis software (3DSYSTEMS, Rock-Hill, S.C., USA). At this point, it is assumed that the mean convergence angle is a mean value of an overall axial wall angulation.

Test 3: Evaluation of Total Surgical Operation that is Reduced as Compared with the Convention Art In A and B of TEST 1, the total surgical operation time from a moment where the operation seats on a unit chair to a surgical operation finish was measured and compared with each other.

Conclusion

1. When the abutment was formed using the three-dimensional space angle correcting apparatus of the present invention, the three-dimensional space angle of the abutment was significantly and statistically reduced as compared with the conventional art. When using the conventional art, the mean three-dimensional space angle was 21-degree. When using the inventive apparatus, the mean three-dimensional space angle of the abutment was 12-degree. When using the inventive apparatus, the dispersion of the three-dimensional space angle is reduced as compared with the conventional art. This allows the operator to accurately and consistently treat the patient.

2. The total surgical operation time was significantly reduced.

As described above, the apparatus and method for correcting the three dimensional space-angle of the dental hand piece drill has the following effects:

According to the exemplary embodiments of the present invention, the three dimensional space-angle of the drill of the dental hand piece can be corrected within a range of the reference three-dimensional space angle, which are not limited in use by an ambient environment while not using the reference body for tracking, an additional camera, and the like.

In addition, according to the exemplary embodiments, the apparatus and method can correct the three dimensional space-angle of the drill for the dental hand piece, which can reduce factors that may disturb the operator by miniaturization and simplification, are not limited in use by a circumferential environment such as the metal prosthetics in the mouth, maintain accuracy, are inexpensive, and intuitional and easy in use.

According to the exemplary embodiments of the present invention, the three dimensional space-angle of the drill of the dental hand piece can be corrected within a range of the reference three-dimensional space angle, which are not limited in use by an ambient environment while not using the reference body for tracking, an additional camera, and the like.

In addition, according to the exemplary embodiments, the apparatus and method can correct the three dimensional space-angle of the drill for the dental hand piece, which can reduce factors that may disturb the operator by miniaturization and simplification, are not limited in use by a circumferential environment such as the metal prosthetics in the mouth, maintain accuracy, are inexpensive, and intuitional and easy in use.

Furthermore, according to the exemplary embodiments of the present invention, since the angle of the dental drill can be calculated in the body unit of the hand piece, the size of the head unit (drill receiving portion) and be reduced and thus miniaturized.

The above-disclosed subject matter is to be considered illustrative and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An apparatus for correcting a three dimensional space-angle of a drill for a dental hand piece for a tooth structure including hard and soft tissues in an oral and maxillofacial area including a jawbone and teeth of a patient, comprising:
    a housing provided on a fixing unit of the dental hand piece;
    a first sensing unit for measuring an angle of the housing in real-time;
    a second sensing unit for measuring an angle of a head portion or jaw of the patient in real-time;
    an operating unit for primarily correcting the angle of the housing measured by the first sensing unit with reference to the angle of the drill and secondarily correcting an angle of the drill, which is primarily corrected, with reference to an angle correcting value of the drill with respect to the tooth structure considering the angle measured by the second sensing unit, thereby calculating a three-dimensional space angle of the drill, wherein
    correcting with respect to the angle of the housing and the angle of the drill is performed by measuring the angle of the dental hand piece and the angle of the head portion or jaw of the patient in real-time, the correction being performed to correct the angle of the drill by measuring the angle of the dental hand piece in real-time using the following algorithm:

$$\begin{bmatrix} x \\ y \\ z \end{bmatrix} = \begin{bmatrix} \cos\theta & 0 & \sin\theta \\ 0 & 1 & 0 \\ -\sin\theta & 0 & \cos\theta \end{bmatrix} \begin{bmatrix} x' \\ y' \\ z' \end{bmatrix}$$

where, the x, y, and z indicate orientation of the drill, the x', y', and z' indicate orientation of the fixing unit of the dental hand piece, and the θ denotes an angle between a first imaginary line extending in a longitudinal direction of the fixing unit and a second imaginary line perpendicular to the drill;
    a setting unit for setting a reference three-dimensional space angle of the drill with respect to the tooth structure according to the correction; and
    a display unit for displaying an alert message when the three-dimensional space angle of the operating unit deviates from a predetermined range of the reference three-dimensional space angle.

2. The apparatus of claim 1, wherein the housing is detachably fixed on the fixing unit of the dental hand piece.

3. The apparatus of claim 2, wherein the housing has a hollow portion that is detachably fitted on the fixing unit of the dental hand piece.

4. The apparatus of claim 1, wherein the housing is integrally formed with the fixing unit of the dental hand piece.

5. The apparatus of claim 3, wherein a vibration-preventing member is provided on an inner circumferential surface of the hollow portion.

6. The apparatus of claim 1, wherein each of the first and second sensing unit is an electronic sensor.

7. The apparatus of claim 6, wherein each of the first and second sensing unit is an electronic sensor having a gyro sensor and an acceleration sensor.

8. The apparatus of claim 1, wherein the display unit comprises a wire or wireless communication module transmitting the alert message to an external terminal.

9. The apparatus of claim 1, wherein the setting unit further comprises a switch; and
    the reference three-dimensional space angle is set as an angle that is set by the operator when the operator presses the switch.

10. The apparatus of claim 9, wherein the switch is provided on a pedal so that the operator steps on the pedal.

11. The apparatus of claim 1, wherein the display unit comprises:
    a first lamp displaying such that the drill is inclined to a right direction that is a +X-axis;
    a second lamp displaying such that the drill is inclined to a lower direction that is a −Y-axis; a third lamp displaying such that the drill is inclined to a left direction that is a −X-axis; and
    a fourth lamp displaying such that the drill is inclined to an upper direction that is a +Y-axis.

12. The apparatus of claim 11, wherein each of the first, second, third, and fourth lamps is provided and having at least one color light.

13. The apparatus of claim 11, wherein the housing is formed in a hollow cylindrical shape;
the first, second, third, and fourth lamps are provided as a one lamp unit
and are disposed along an outer circumference of the housing at a predetermined distance.

14. A method for correcting a three dimensional space-angle of a drill for a dental hand piece for a tooth structure comprising hard and soft tissues in an oral and maxillofacial area comprising a jawbone and teeth of a patient, comprising:
measuring an angle of the dental hand piece and an angle of a head portion or jaw of the patient in real-time;
calculating the three-dimensional space angle of the drill by primarily correcting the angle of the dental hand piece as an angle of the drill and secondarily correcting an angle the drill, which is primarily corrected, with reference to an angle correcting value of the drill with respect to the tooth structure considering the angle of the head portion, wherein
correcting with respect to the angle of the dental hand piece and the angle of the drill is performed by measuring the angle of the dental hand piece and the angle of the head portion or jaw of the patient in real-time, the correction being performed to correct the angle of the drill by measuring the angle of the dental hand piece in real-time using the following algorithm:

$$\begin{bmatrix} x \\ y \\ z \end{bmatrix} = \begin{bmatrix} \cos\theta & 0 & \sin\theta \\ 0 & 1 & 0 \\ -\sin\theta & 0 & \cos\theta \end{bmatrix} \begin{bmatrix} x' \\ y' \\ z' \end{bmatrix}$$

where, the x, y, and z indicate orientation of the drill, the x', y', and z' indicate orientation of the fixing unit of the dental hand piece, and the $\theta$ denotes an angle between a first imaginary line extending in a longitudinal direction of the fixing unit and a second imaginary line perpendicular to the drill;

setting a reference three-dimensional space angle of the drill with respect to the tooth structure according to the correction; and
displaying an alert message when the calculated three-dimensional space angle deviates from a predetermined range of the reference three-dimensional space angle.

15. The method of claim 14, wherein, in the displaying of the alert message,
the alert message is displayed such that, when the three-dimensional space angle deviates from the predetermined range of the reference three-dimensional space angle as the drill is inclined to a right direction that is a +X-axis, the drill is inclined to a left direction that is a −X-axis;
the alert message is displayed such that, when the three-dimensional space angle deviates from the predetermined range of the reference three-dimensional space angle as the drill is inclined to a lower direction that is a −Y-axis, the drill is inclined to an upper direction that is a +Y-axis;
the alert message is displayed such that, when the three-dimensional space angle deviates from the predetermined range of the reference three-dimensional space angle as the drill is inclined to the left direction that is the −X-axis, the drill is inclined to the right direction that is the +X-axis; and
the alert message is displayed such that, when the three-dimensional space angle deviates from the predetermined range of the reference three-dimensional space angle as the drill is inclined to the upper direction that is the +Y-axis, the drill is inclined to the lower direction that is the −Y-axis.

16. The method of claim 15, wherein, when the three-dimensional space angle of the drill is inclined in a first side and thus deviates from the predetermined range of the reference three-dimensional space angle, in order to incline a blade in a second side opposite to the first side, one of lamps, which has a first color and disposed at the second side, keeps emitting light and another one of the lamps, which has the first color and disposed on the first side, keeps blinking.

17. The method of claim 14, wherein the displaying of the alert message comprises transmitting the alert message to an external message through a wire or wireless communication.

\* \* \* \* \*